(12) United States Patent
Armour (10) Patent No.: US 6,706,480 B1
(45) Date of Patent: Mar. 16, 2004

(54) GENETIC SCREENING

(75) Inventor: John Anthony Armour, Nottingham (GB)

(73) Assignee: University of Nottingham, Nottingham (GB)

( * ) Notice: Subject to any disclaimer, the term of this patent is extended or adjusted under 35 U.S.C. 154(b) by 0 days.

(21) Appl. No.: 09/914,811

(22) PCT Filed: Mar. 3, 2000

(86) PCT No.: PCT/GB00/00761

§ 371 (c)(1),
(2), (4) Date: Jan. 3, 2002

(87) PCT Pub. No.: WO00/53804

PCT Pub. Date: Sep. 14, 2000

(30) Foreign Application Priority Data

Mar. 5, 1999 (GB) ............................................... 9904991

(51) Int. Cl.⁷ ........................... C12Q 1/68; C12P 19/34; C07H 21/02; C07H 21/04
(52) U.S. Cl. ......................... 435/6; 435/91.2; 536/23.1; 536/24.3
(58) Field of Search ................... 435/6, 91.2; 536/23.1, 536/24.3

(56) References Cited

U.S. PATENT DOCUMENTS 5,601,976 A * 2/1997 Yamane
5,770,372 A * 6/1998 Concannon
5,942,391 A * 8/1999 Zhang et al.

OTHER PUBLICATIONS

International Application Published Under Patent Cooperation Treaty,Publication WO 00/53804 A3, International Publication Date 14.09.001.

Armour et al., "Measurement Of Locus Copy Number by Hybridisation with Amplifiable Probes", vol. 28, No. 2, 2000, pp. 605–609.

WO 93 04199 A (Scient Generics Ltd), Mar. 4, 1993.

WO 99 06042 A (Holmes Michael John: Dynal , Jun. 14, 1990.

WO 99 07892 A (Univ California), Feb. 18, 1999.

WO 00 43538 A (Univ Montreal; Brukner Ivan et al.), Jul. 27, 2000.

WO 98 15649 A (Cremer Thomas et al.), Apr. 16, 1998.

Hill J.M. et al., "Quantitative Analysis of Polymerase Chain Reaction Products by Dot Blot", Analytical Biochemistry, US Academic Press, Vo. 235, No. 1, Mar. 1, 1996, pp. 44–48.

Reischul U et al., "Quantitative PCT A Survey of the Present Technology", Molecular Biotechnology, vol. 3, 1995, pp. 55–71.

WO 95/25538 (General Hospital Corporation), Sep. 28, 1995.

* cited by examiner

*Primary Examiner*—Ethan Whisenant
(74) *Attorney, Agent, or Firm*—Watts, Hoffmann, Fisher & Heinke Co., LPA (57) ABSTRACT

A method of screening for nucleic acid sequence copy no. in a sample genetic material, the method including introducing a no. of different genetic probes to hybridize with the genetic sample. The probes are flanked by the same or substantially the same primer binding sites thereby enabling amplification of sample-bound probes using a single primer pair and thus the screening of different sequence copy nos. at the same time. Genetic alterations are known to underlie phenotype characteristics including disorders as idiopathic mental retardation and neoplasia.

24 Claims, 6 Drawing Sheets

```
                        primer PZA
             AGTAACGGCCGGCCAGTGTGCTG          EcoRV
GGATCCACTAGTAACGGCCGGCCAGTGTGCTGGAATTCTGCAgatatcCATCACACTGGCGCCGCTCGAGCA
+----+----+----+----+----+----+----+----+----+----+----+----+----+----+
CCTAGGTGATCATTGCCGGCCGGTCACACGACCTTAAGACGTctatagGTAGTGTGACCGCGGCGAGCTCGT
                                             GTAGTGTGACCGCGGCGAGC
                                                primer PZB
```

FIG. 6

SEQUENCE LISTING

<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: Description of Articifical Sequence: Primer.
      Part of vector sequence for the pZero-2 cloning vector (full
      sequence for the vector available from
      http://www.invitrogen.com/vecseq_gcg/pzero2.seq)

<400> SEQUENCE: 1
agtaacggcc gccagtgtgc tg                                          22

<210> SEQ ID NO 2
<211> LENGTH: 21
<212> TYPE: DNA
<213> ORGANISM: Artificial
<220> FEATURE:
<223> OTHER INFORMATION: Description of Articifical Sequence: Primer.
      Part of vector sequence for the pZero-2 cloning vector
      (full sequence for the vector available from
      http://www.invitrogen.com/vecseq_gcg/pzero2.seq)

<400> SEQUENCE: 2
cgagcggccg ccagtgtgat g                                           21

<210> SEQ ID NO 3
<211> LENGTH: 20
<212> TYPE: DNA
<213> ORGANISM: Homo sapiens

<400> SEQUENCE: 3
gcagtagagc agtcagggag                                             20

<210> SEQ ID NO 4
<211> LENGTH: 23
<212> TYPE: DNA
<213> ORGANISM: Homo sapiens

<400> SEQUENCE: 4
ggggagagaa agaaacaagt ttg                                         23

GENETIC SCREENING

The present invention relates to screening for sequence copy number and in particular to screening for changes in copy number of a plurality of nucleic acid sequences substantially simultaneously.

The loss or reduction in the normal number of copies of a genetic sequence (deletion) or the increase in copy number (amplification) are of widespread general importance. Such genetic alterations are known to underlie phenotype characteristics both somatic and germline including disorders as diverse as idiopathic mental retardation and neoplasia. The demonstration of the site and nature of such genetic alteration is critical in the identification of the genes responsible and to the development of appropriate and effective treatments and therapies.

In principle, it is possible to screen for genetic deletions by using Southern blot hybridisation. However, this method requires heterozygosity, and whilst the loss of heterozygosity at polymorphic loci can be used to demonstrate the absence of one allele in the soma or in the germline, its effectiveness is limited by the requirement for heterozygosity and the number of repeated tests needed to screen even a small fraction of the genome.

If sufficient precautions are taken to assure quantitative yields, the polymerase chain reaction (PCR) can be used to screen for copy number, and specialised systems have been developed to assure quantitative PCR by following the accumulation of products as amplification proceeds. However, such systems do not provide for the satisfactory analysis of a plurality of alterations substantially simultaneously.

According to the present invention there is provided a method of screening for copy number of target nucleic acid sequences in a sample of genetic material, the method comprising introducing to the sample a plurality of different genetic probes suitable to hybridise with respective target sequences and all flanked by the same or substantially the same primer binding sites, subjecting the sample to conditions favouring hybridisation of the probes to their respective sequences, and amplification of sample-bound probes using a pair of primers, wherein analysis of the respective amounts of amplified probe provides for quantitative determination of the copy number of the respective nucleic acid sequences in the sample.

Preferably each probe is distinguishable from the other (s), for example by having distinguishing mobility characteristics through a separating gel. Preferably the plurality of different probes comprises a predetermined set of different probes each chosen to be specific for a respective target nucleic acid sequence. The set may comprise probes suitable to screen a plurality of different nucleic acid sequences simultaneously or substantially simultaneously such that determination of the quantity of each probe product produced, preferably using the polymerase chain reaction (PCR), enables quantitative determination of the copy number of the respective sequences in the sample. The method may be used to screen sequences of different genes or different sequences within a gene, such as different exons in a eukaryotic gene. Preferably the method is used to detect genetic alterations such as genetic deletions (reduction in sequence copy number) and genetic amplification (increase in sequence copy number).

Preferably the genetic material is immobilised prior to hybridisation, such that hybridised flanking primers are likewise immobilised. Preferably an excess of probes is used.

Probes labelled for ready identification, such as with fluorescent labels are preferably used. More than one set of probes may be used, either simultaneously or sequentially. The flanking primer pairs may be the same or different for each set of probes.

Preferably the method comprises means to obviate or mitigate hybridisation between primer binding sequences. Competing oligonucleotides may be introduced to the sample preferably during the hybridisation stage to releasably bind to the primer binding sites flanking each probe whereby to mitigate primer binding site interactions.

Preferably unbound probes and primers are thoroughly washed away from the bound probes following hybridisation stage and prior to analysis.

The method may be used to screen DNA, RNA and/or cDNA with appropriate probe sets. The method may be used to screen somatic and/or germline sequences. The method may be used to screen for polymorphic alterations.

The invention further provides a set of probes substantially as described above in any of the preceding seven paragraphs.

The invention may still further comprise a kit for such a method described above in any of the preceding eight paragraphs, which kit comprises a probe set generally as defined above, amplification primers and means to enable amplification and analysis of amplification product(s).

BRIEF DESCRIPTION OF THE DRAWINGS

The present invention will now be described by way of example only with reference to the accompanying drawings, in which.

Figure 1:
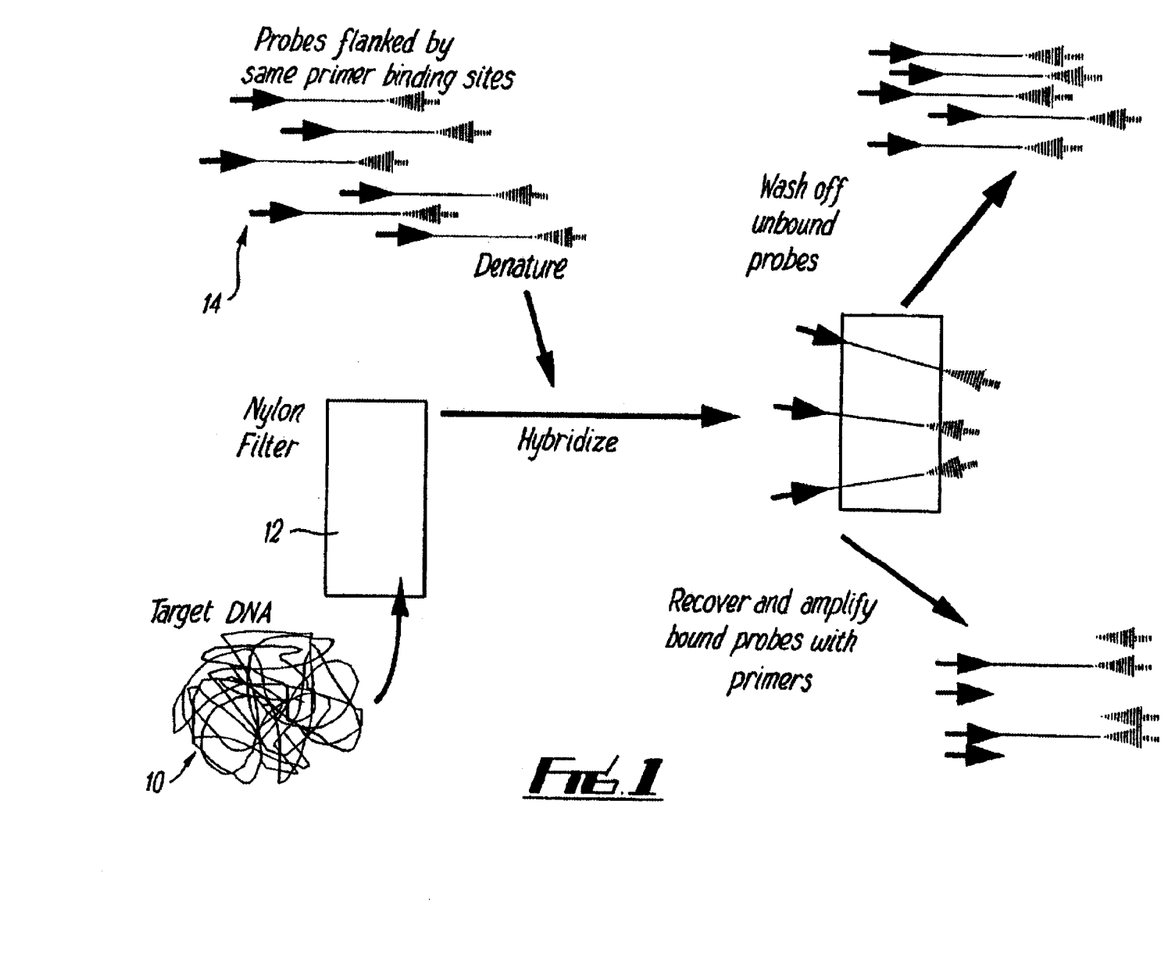
FIG. 1 is a simple schematic illustration of a method according to the invention.

With reference to FIG. 1, there is provided a method of screening for copy number of target nucleic acid sequences in a sample of genetic material, the method comprising introducing to the sample a plurality of different genetic probes suitable to hybridise with respective target sequences and all flanked by the same or substantially the same primer binding sites, subjecting the sample to conditions favouring hybridisation of the probes to the respective sequences, and amplification of sample-bound probes using a pair of flanking primers, wherein analysis of the respective amounts of amplified probe provides for quantitative determination of the copy number of the respective nucleic acids sequences in the sample.

The method can be used to screen for genetic alterations, in particular deletions and amplifications in copy number of genetic sequences, both somatic and germline.

The sample of genetic material to be screened, which may comprise, DNA, cDNA and/or RNA, shown diagrammatically in FIG. 1 (10), is reversibly immobilised on a medium (12) such as a nylon filter.

A plurality of probes (14) is designed and prepared to seek out and hybridise with specific nucleic acid sequences, if present in the sample. The probes (14) are chosen to comprise a set of different probes each type operable to seek out a different respective nucleic acid sequence which may be sequences suspected of being involved in a particular disorder or condition for example, in the organism from which the sample has been taken. Alterations in the copy number of particular genetic sequences are known to be involved in conditions such as cancer and mental retardation, and probes specific for these sequences can be prepared and comprised in a probe set used in accordance with the present methodology for example where certain symptoms suggest these disorders or diseases may be involved.

When an appropriate probe set is created or identified, it is then introduced to the immobilised genetic material in stoichiometric excess under conditions favouring hybridisation of the probes to their respective nucleic acid sequences, if present.

Once sufficient time has elapsed to provide for hybridisation, unbound probes are washed thoroughly away and the PCR employed to amplify bound probes.

The use of the same primer pair binding sites flanking all the different probes is important to the successful operation of this method, and allows different bound probes to be amplified together with a single primer pair and thus the screening for a plurality of different loci at the same time.

Some interaction has been experienced between primer binding sites flanking different probes, but this problem has been addressed by adding to the hybridisation solution an excess of competing oligonucleotides which releasably bind to the respective primer binding sites thereby preventing such undesirable interactions whilst not adversely affecting the subsequent amplification process. The oligonucleotides are displaced once hybridisation of the probes to the sample is complete, to provide for hybridisation of the amplification primers to the binding sites.

Figure 6:
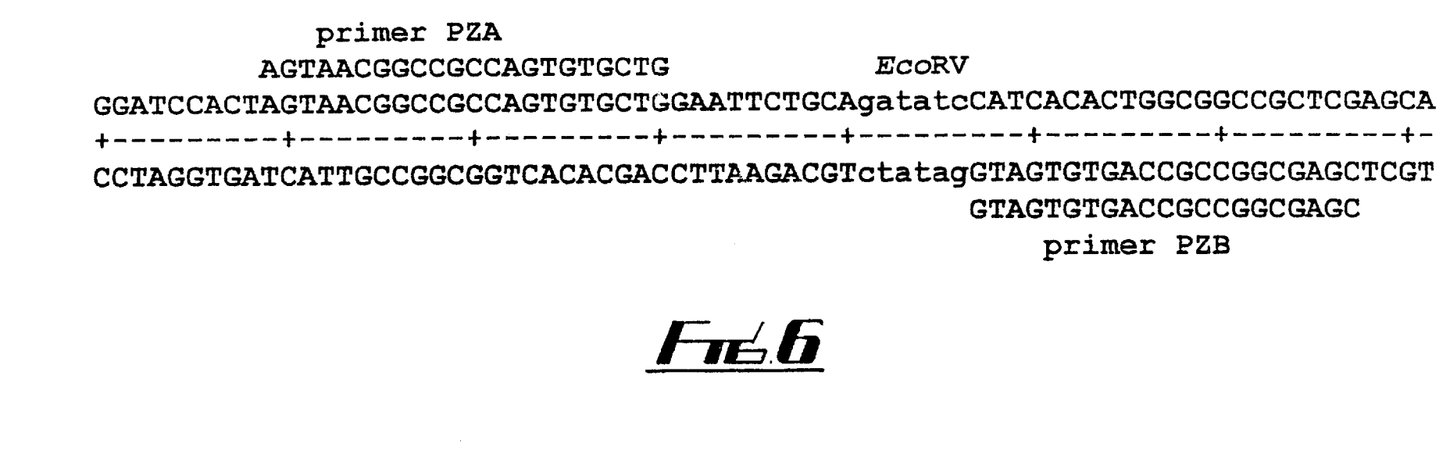
FIG. 6 shows the EcoRV cloning site of pZero2 and the corresponding primer combination (PZA and PZB) used to generate probes from fragments cloned into the EcoRV site.

Respective sets of probes can be made either by ligation to oligonucleotide adapters, or more simply by preparing the probes as inserts into the same site of a cloning vector, and using primers flanking the cloning site for amplification. FIG. 6 shows the cloning site of the vector pZero2 (sequence provided by InVitrogen: http://www.invitrogen.com/vecseq-gcg/pzero2.seq), showing the primers PZA and PZB flanking the EcoRV site (lowercase) used to clone blunt-ended fragments. Products amplified using these primers are therefore 59 bp longer than the cloned inserts. It is thus possible to prepare sets of probes, each detecting a different locus, but all flanked by the same primer-binding sites.

It is important that a probe set is created such that each contributing probe is distinguishable, for example by virtue of its mobility through a separating gel. Following amplification, the appearance of a product of corresponding mobility acts to report the presence of a particular nucleotide sequence, and hence the presence of that sequence in the target sample. As an excess of probe is used, and amplification is restricted to the quantitative phase, the absolute amount of each product reflects it copy-number in the sample tested. Different probes may amplify with different efficiencies, but the proportional contribution from each probe will reflect its dosage in the sample and can be inferred from comparisons between different samples examined with the same probe set. As it is the retained probe that is amplified, not the sample, the gel mobility of the product is not influenced by the presence (for example) of Restriction Fragment Length Polymorphisms (RFLPs) at that locus.

The following outlines experiments conducted using the method of the present invention to screen a plurality of different genetic sequences simultaneously. A set of 43 amplifiable probes was generated by cloning blunt-ended fragments into the EcoRV site of pZero2 (FIG. 6), followed by amplification with vector primers flanking this site, and selection of a mix of probes of different lengths. This mix included probes from 7 autosomes (1, 5, 11, 16, 17, 18 and 22), as well as the X and Y chromosomes.

The initial mix of 43 probes was subcloned from plasmids and plasmid fragments known from sequencing or hybridisation not to contain dispersed repeat elements; in the case of one of the Y-linked probes (SRY), a 1360 bp fragment was amplified using primers SRYA, SEQ ID NO: 3, (5'GCAGTAGAGCAGTCAGGGAG3') and SRYB, SEQ ID NO: 4, (5'GGGGAGAGAAAGAAACAAGTTTG3'). Other sources of cloned genomic DNA were: chromosome 1, pJBT2 (JALA, unpublished); chromosome 17, pYNZ22 (Nakamura et al., 1988); chromosome 18, pMS440 (Armour et al., 1990); chromosome 22, pMS632c (Armour et al., 1995); chromosome X, pMS613 (Armour et al., 1990). After isolation of the genomic insert and digestion with frequently-cutting restriction enzymes producing blunt ends (generally double digestion with AluI plus HaeIII), the resulting smaller fragments were cloned into the EcoRV site of pZero2 (InVitrogen) and propagated in *E. coli* TOP10 (In Vitrogen). Care was taken to avoid repeat regions in DNA from minisatellite containing clones.

With reference to FIG. 6, probes prepared by cloning blunt-ended restriction fragments from primary clones into the EcoRV site of pZero2 (In Vitrogen) were amplified directly from bacterial cells (Sandhu et al., 1989) using flanking vector primers PZA, SEQ ID NO: 1, (5'AGTAACGGCCGCCAGTGTGCTG3') and PZB, SEQ ID NO: 2, (5'CGAGCGGCCGCCAGTGTGATG3'). The positions of these primers in the pZero-2 cloning site is shown in FIG. 6. PCR was carried out in Advanced Biotechnologies Buffer IV (75 mM Tris-HCl pH8.8, 20 mM $(NH_4)_2SO_4$, 0.01% Tween), with 0.2 mM each dNTP, 1 mM $MgCl_2$, 0.2 µM each primer and 0.05 U/µl Taq DNA polymerase (Advanced Biotechnologies). Reactions (generally 10 µl) were subjected to 25 cycles of (95° C. for 1 minute/70° C. for 1 minute). Products amplified using $^{33}P$ end-labeled PZA were separated on denaturing 6% polyacrylamide/50% urea gels and probe mixes assembled such that the mobilities of all probes were distinct.

Sample DNA for immobilisation was prepared in an initial volume of less than 5 µl, denatured by addition of 1 µl 1M NaOH, and spotted onto a nylon filter (MSI MAGNA, approximate dimensions 2 mm×4 mm), 1 µl at a time, allowing the solution to dry between applications. When all the DNA had been added the DNA was irreversibly bound to the filter using U.V. irradiation. Since numerous filters were to be used in the same hybridisation, individual marks cut into the edges and corners made clear the identity of each filter.

Filters were prehybridised in 1 ml of prehybridisation solution (0.5M sodium phosphate pH7.2, 7% SDS, 0.1 mg/ml alkali-denatured herring sperm DNA) at 65° C. overnight, and before hybridisation this was exchanged for 200 µl of prehybridisation solution with the addition of denatured human Cot-1 DNA (Gibco BRL) to a final concentration of 10 µg/ml. Probe mixtures containing about 100 pg of each sequence in 1 µl were mixed with 7 µg *E. coli* DNA (DH5' DNA, digested with HaeIII) and 1 µg human Cot-1 DNA (Gibco-BRL), and denatured by adding 2 µl 1M NaOH. After 1 minute at 37° C., the probe mixture was placed on ice, neutralized by adding 3 μl 1M $NaH_2PO_4$, and added to the hybridisation solution.

Hybridisation was left to proceed at 65° C. overnight, and the filters were thoroughly washed at 65° C. in (a) two 1 ml changes of prehybridisation solution, (b) 200 ml 1×SSC/1% SDS and (c) 500 ml 0.1×SSC 0.1% SDS. Washed filters were then transferred to individual 50 μl amplification reactions (constituents as for probe amplification), and bound DNA amplified for 5 cycles of 95° C. 1 minute/70° C. 1 minute.

This low-level preamplified solution was then used to seed further 10 μl amplifications using $^{33}P$ 5' end-labelled primer PZA. Labelled PCR products were given a final incubation at 72° C. for 20 minutes (to drive to completion the addition of untemplated A at the 3' ends), an equal volume of formamide dye mix (98% formamide, 10 mM EDTA pH 8.0, 1 mg/ml xylene cyanol FF, 1 mg/ml bromophenol blue) added, and the DNA denatured at 100° C. for 2 minutes and then placed on ice. From this denatured sample, 4 μl was loaded into a well of a 6% polyacrylamide/50% urea gel in 0.5×TBE, and the gel run at 90W (to maintain a gel temperature of about 45° C.) until the xylene cyanol dye was close to the end of the gel. Gels were fixed in 10% methanol/10% acetic acid, dried, and radioactivity detected either by standard autoradiography or (for quantitative analysis) using ImageQuant software analysis on data captured by a storage phosphorimager screen (Molecular Dynamics).

Figure 2:
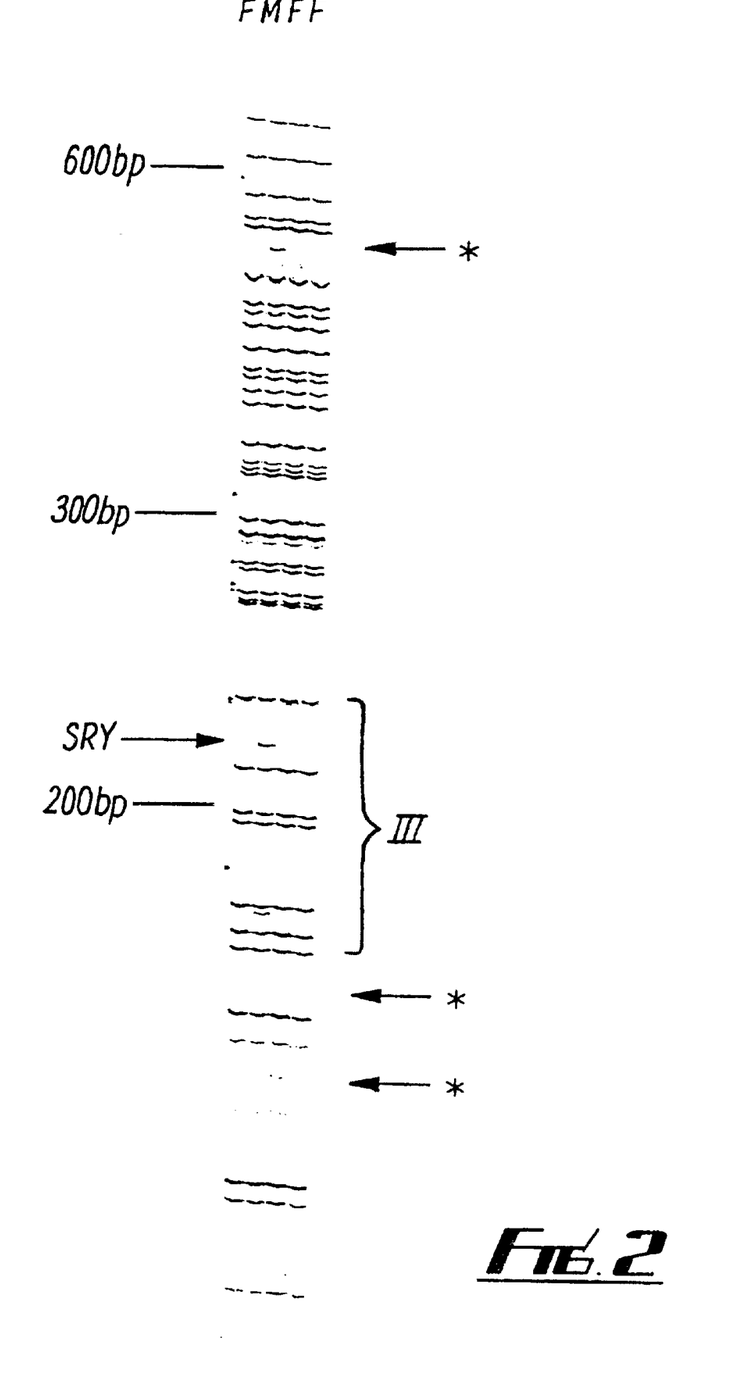
FIG. 2 shows a gel run produced from samples from four unrelated humans using the method according to the present invention.
Figure 3:
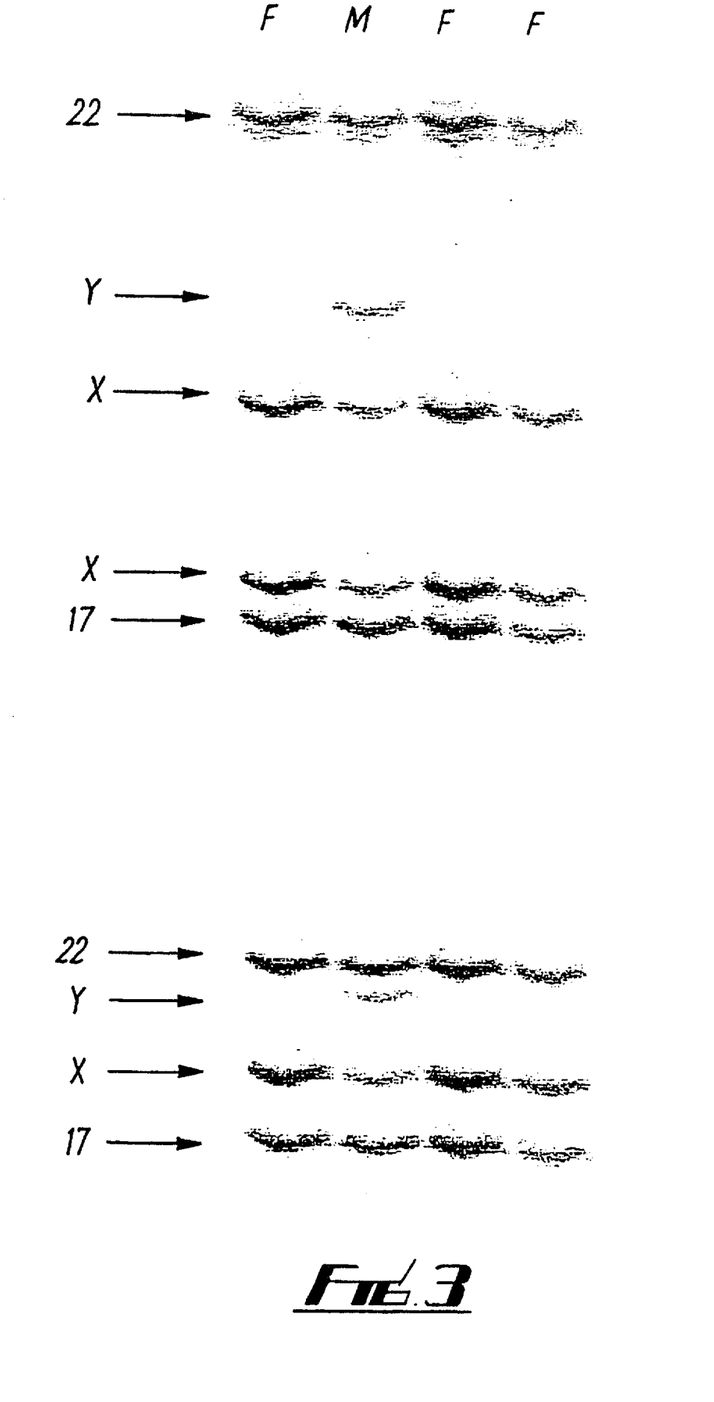
FIG. 3 shows an enlargement of the central region III of the gel in FIG. 2.
Figure 4:
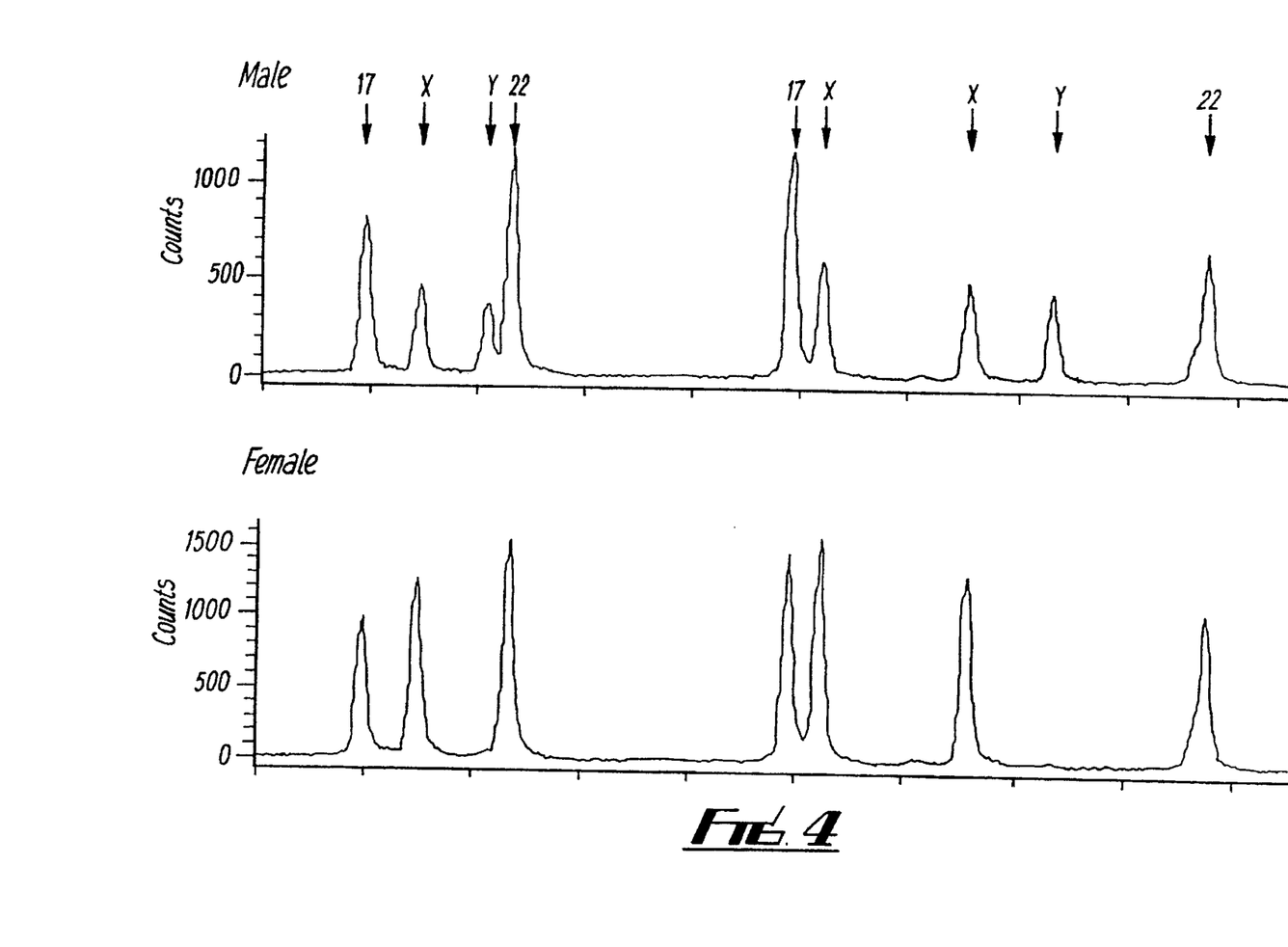
FIG. 4 shows the results of quantitative analysis of the region III of the gel from one male sample (upper trace) and one female (lower trace)

The screening results of hybridising this probe set with DNA from one male and three females is shown in FIG. 2. The autosomal loci give comparable signals, between all individuals; while there is probe-to-probe variation in absolute intensity, the relative contribution of each band to the whole is highly reproducible. By contrast, the Y-derived probes only give strong signals in the hybridisation with male DNA. The relative signal from the X-linked probes is reduced by about 50% in the male (FIGS. 3 and 4).

Figure 5:
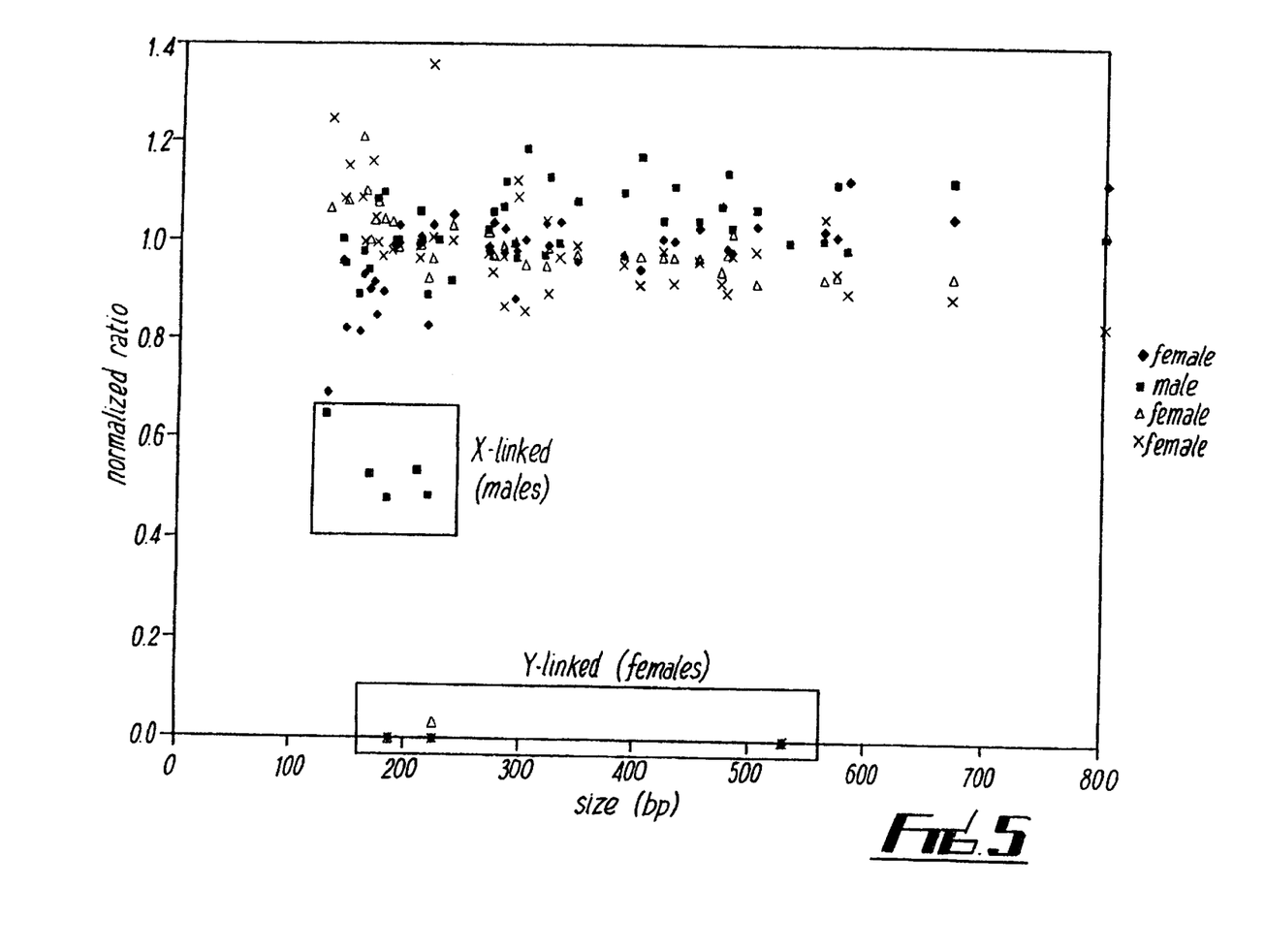
FIG. 5 shows the relative signal from different probes shown plotted against probe size.

In FIG. 5, the normalised relative signal from each probe is shown plotted against the length of the probe; signal intensities are normalised relative to the mean value for that probe among all individuals tested for autosomal loci, among all the females for X-linked probes and relative to the male for Y-linked probes. The boxed points are the points for X-linked loci in the male (about 50% signal intensity) and for Y-linked probes in females (close to zero). This experiment models the expected detection of homozygous deletions (Y-linked loci in females) or hemizygous deletions (X-linked loci in males). In the size range 140–600 bp the signal appears to reflect copy number variation consistently.

Nearly all the amplified bands seen after hybridisation corresponded in size with the expected probes. There were however three bands (marked with asterisks on FIG. 2) which did not correspond to probes of known origin; the largest of these is clearly Y-linked. The simplest explanation for the appearance of these bands is that they are the result of contamination of the probe mix by other probes made at the same time. Since (if hybridisation has gone to near completion) the intensity of the band recovered from a target DNA will depend on its copy-number in the target DNA, and not on its concentration in the probe mix, even relatively minor contamination with additional probes could result in the appearance of unexpected bands in the amplified product at intensities equal to the predicted bands. Probe fragments corresponding to two of these additional bands are detectable as components of the initial probe mix. The importance of avoiding even minor contamination with additional probes represents an advantage of isolating and storing the probes as clones (rather than PCR products), since uncontaminated probe preparations can be reconstituted from colony-purified clones.

The efficiency of this method derives from its ability to examine numerous loci simultaneously (in this experiment, 43 probes). In the format used here, in which radiolabelled probes are resolved using denaturing polyacrylamide gel electrophoresis, the number of probes which can be analysed simultaneously is limited only by the resolving power of the gel. Since probes in the size range 140–600 bp have been used successfully in this experiment, careful size-selection of probes could lead to probe sets containing more than a hundred probes, which might (for example) be used as chromosome-specific subsets to analyse copy number at megabase resolution.

Moreover, greater resolution may be achieved using fluorescently-labelled probes and apparatus and software designed for automated sequence analysis. This would not only have the advantage of single-base resolution over a larger range (and hence the possibility of more probes per lane), but could also use multiple fluors in a single track. Thus if (for example) four sets of each of 100 probes were assembled, the probes of each set flanked by different primer binding sites (same within a set), they could be hybridised With the same target, and after the initial recovery of bound probes and low-level preamplification using all primer pairs, each set could be selectively amplified with its own primer pair (one fluorescent), and the four resulting sets of fluorescent products mixed and run in the same lane. Similarly, if the same primer was available with different fluorescent labels, then a direct comparison between two samples (for example tumour versus normal from the same person) could be made by labelling the products from each with different fluors and running in the same lane of the gel.

In the present format, the high resolution of polyacrylamide gel electrophoresis allows the simultaneous differentiation of products from many different loci, but even using all the available "slots" with judicious assembly of probe sets, this format probably limits the number of probes flanked by a given primer pair which can be resolved in one lane to about 500, and hence if four probe sets with different flanking primers can be used simultaneously, fewer than 2000 probes can be examined simultaneously in this test. It might be possible to augment the resolution of this analysis by using formats for the quantitative detection of amplified probe which do not rely on gel electrophoresis. One alternative would be to use recovered probes to label arrays of the clones from which the probes themselves were produced; a procedure analogous to array-CGH (Pinkel et al., 1998), but with the added efficiency that the method according to the present invention the MAPH has already produced proportionate amounts of the relevant single-copy probes from the genomic targets, reducing the complexity of the mixture (for increased speed of hybridisation) and by avoiding multi-copy sequences, presumably allowing quantification with a greater signal:noise ratio.

The experiments explained here have used genomic DNA as the target nucleic acid, but an extension of this method would be to use probes to probe RNA (or cDNA) for highly parallel analysis of gene expression. Current RT-PCR based methods for quantification of gene expression do not allow the simple analysis of numerous loci simultaneously.

The method could be used to screen for alterations to a plurality of sequences relating to different genes, and/or sequences within a target gene e.g. screen for alterations in exon copy number within a eukaryotic gene.

Using the method according to the present invention to detect deletions and amplifications in (for example) idiopathic mental retardation (IMR) assumes that the absence of a locus is abnormal, rather than resulting from a polymorphism. This can be most simply investigated by analysis of the parents in cases of IMR, but it remains possible that wider application of this technique will uncover loci at which there are presence/absence polymorphisms. If enough (sufficiently informative) loci of this kind were available, then assembly of such probes into a mutually compatible "polymorphic set" would allow simultaneous genotyping at (say) 50–100 loci in a single lane of a sequencing gel;

combined with analysis of mixed DNA samples, such a system could provide very high throughput for genotyping without the need for investment in expensive or complicated equipment.

Whilst endeavouring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

What is claimed is:

1. A method of screening for copy number of target nucleic acid sequences in a sample of genetic material, the method comprising introducing to the sample a plurality of different genetic probes suitable to hybridise with respective target sequences and all flanked by the same or substantially the same primer bonding sites, subjecting the sample to conditions favoring hybridization of the probes to their respective sequences, and amplification of sample-bound probes using a pair of primers, wherein analysis of the respective amounts of amplified probe provides for quantitative determination of the copy number of the respective nucleic acid sequences in the sample.

2. A method according to claim 1, characterized in that each probe is distinguished from the other(s).

3. A method according to claim 1, characterized in that each probe is distinguished from the other(s) by having distinguishing mobility characteristics through a separating gel.

4. A method according to claim 1, characterized in that the plurality of different probes comprises a predetermined set of different probes each chosen to be specific for a respective target nucleic acid sequence.

5. A method according to claim 4, characterized in that the set comprises probes suitable to screen a plurality of different nucleic acid sequences simultaneously or substantially simultaneously such that determination of the quantity of each probe product produced enables quantitative determination of the copy number of the respective sequences in the sample.

6. A method according to claim 1, characterized in that the polymerase chain reaction is used to determine the quantity of each probe product produced.

7. A method according to claim 1, characterized in that the method is used to screen sequences of different genes or different sequences within a gene.

8. A method according to claim 1, characterized in that the method is used to screen sequences of different exons in a eukaryotic gene.

9. A method according to claim 1, characterized in that the method is used to detect genetic alterations.

10. A method according to claim 1, characterized in that the method is used to detect genetic deletions (reductions in sequence copy number) or genetic amplification (increases in sequence copy number).

11. A method according to claim 1, characterized in that the genetic material is immobilized prior to hybridization, such that hybridization flanking primers are likewise immobilized.

12. A method according to claim 1, characterized in that an excess of probes is used.

13. A method according to claim 1, characterized in that probes labelled for ready identification are used.

14. A method according to claim 1, characterized in that probes labelled with fluorescent labels are used.

15. A method according to claim 4, characterized in that more than one set of probes is used, either simultaneously or sequentially.

16. A method according to claim 4, characterized in that more than one set of probes is used and flanking primer pairs are the same for each set of probes.

17. A method according to claim 4, characterized in that more than one set of probes is used and flanking primer pairs are different for each set of probes.

18. A method according to claim 1, characterized in that the method comprises means to obviate or mitigate hybridization between primer binding sequences.

19. A method according to claim 1, characterized in that competing oligonucleotides are introduced to the sample.

20. A method according to claim 1, characterized in that competing oligonucleotides are introduced to the sample during the hybridization stage to releasably bind to primer binding sites flanking each probe to mitigate primer binding site interactions.

21. A method according to claim 1, characterized in that unbound probes and primers are thoroughly washed away from bound probes following hybridization and prior to analysis.

22. A method according to claim 1, characterized in that the method is used to screen one or more of DNA, RNA and cDNA with appropriate probe sets.

23. A method according to claim 1, characterized in that the method is used to screen one or more of somatic and germline sequences.

24. A method according to claim 1, characterized in that the method is used to screen for polymorphic alterations.

* * * * *